United States Patent
Lundh et al.

(10) Patent No.: US 9,636,208 B2
(45) Date of Patent: May 2, 2017

(54) VASCULAR PROSTHESES

(75) Inventors: Torbjörn Lundh, Billdal (SE); Erney Mattsson, Västra Frölunda (SE)

(73) Assignee: Y-GRAFT AB, Billdal (SE)

( * ) Notice: Subject to any disclaimer, the term of this patent is extended or adjusted under 35 U.S.C. 154(b) by 1153 days.

(21) Appl. No.: 12/153,087

(22) Filed: May 14, 2008

(65) Prior Publication Data

US 2008/0294245 A1   Nov. 27, 2008

Related U.S. Application Data

(60) Provisional application No. 60/939,250, filed on May 21, 2007.

(30) Foreign Application Priority Data

May 14, 2007   (SE) ...................................... 0701152

(51) Int. Cl.
   *A61F 2/06*   (2013.01)
(52) U.S. Cl.
   CPC .......... *A61F 2/06* (2013.01); *A61F 2002/065* (2013.01); *A61F 2002/068* (2013.01); *A61F 2250/0039* (2013.01)
(58) Field of Classification Search
   CPC ........................................................ A61F 2/06
   USPC ...................... 623/1.35, 1.16, 1.1, 1.13, 1.31
   See application file for complete search history.

(56) References Cited

U.S. PATENT DOCUMENTS

| 6,149,682 | A | * | 11/2000 | Frid | ............................. 623/1.35 |
| 6,454,796 | B1 | | 9/2002 | Barkman et al. | |
| 6,524,336 | B1 | | 2/2003 | Papazolgou et al. | |
| 2002/0058991 | A1 | | 5/2002 | Schmitt | |
| 2006/0116753 | A1 | | 6/2006 | Walsh et al. | |

(Continued)

FOREIGN PATENT DOCUMENTS

| EP | WO 02/24114 | 3/2002 |
| EP | 1645245 | 4/2006 |
| WO | WO 98/06356 | 2/1998 |

(Continued)

OTHER PUBLICATIONS

International Search Report dated Aug. 20, 2009.

(Continued)

*Primary Examiner* — Matthew Schall
(74) *Attorney, Agent, or Firm* — Harness, Dickey & Pierce, P.L.C.

(57) ABSTRACT

A vascular prosthesis is disclosed, comprising a forked tube, having: an inflow tube with an inflow end; a primary distal outflow branch with a primary distal outflow end; and a secondary proximal outflow branch with a secondary proximal outflow end. The two outflow ends are directed in different directions and the two outflow branches in the vicinity of the bifurcation have different cross-sectional areas. Further, the secondary proximal outflow branch is more curved than the primary distal outflow branch, and the secondary proximal outflow branch in the vicinity of the bifurcation has a smaller cross-sectional area than the primary distal outflow branch. Hereby, energy losses at flow bifurcations is adapted to the bypass situation to even out the level of shear stress, thereby avoiding areas with low shear stress and decreasing the tendency for turbulent flow, thus reducing the risk of graftstenosis.

23 Claims, 5 Drawing Sheets

(56) References Cited

U.S. PATENT DOCUMENTS

2006/0287704 A1    12/2006    Hartley et al.

FOREIGN PATENT DOCUMENTS

| WO | WO 2005/004752 | 1/2005 |
|---|---|---|
| WO | 2006/100659 | 9/2006 |

OTHER PUBLICATIONS

Murray, C., "The Physiological Principle of Minimum Work, I. The Vascular System and the Cost of Blood Volume," *Physiology*, vol. 12, pp. 207-214, Jan. 26, 1926.

Murray, C., "The Physiology Principle of Minimum Work Applied to the Angle of Branching of Arteries," The Journal of General Physiology, pp. 835-841, Apr. 1, 1926.

Woldenberg, M. et al., "Relation of Branching Angles of Optimality for Four Cost Principles," pp. 187-204, Feb. 22, 1986.

Zamir, M., "Nonsymmetrical Bifurcations in Arterial Branching," J. Gen. Physiol., vol. 72, pp. 837-845, Dec. 1978.

Bassiouny, H. et al., "Flow Regulation of 72-kD Collagenase IV (MMP-2) After Experimental Arterial Injury," pp. 157-163, Jul. 14, 1998.

Fillinger, M. et al., "Beneficial Effects of Banding on Venous Intimal-Media Hyperplasia in Arteriovenous Loop Grafts," The American Journal of Surgery, vol. 158, pp. 87-94, Aug. 1989.

Geary, R. et al., "Time Course of Flow-Induced Smooth Muscle Cell Proliferation and Intimal Thickening in Endotheialized Baboon Vacsular Grafts," Circulation Research, vol. 74, No. 1, pp. 14-23, Jan. 1994.

Mattsson, E. et al., "Increased Blood Flow Induces Regression of Intimal Hyperplasia," Arteriosclerosis, Thrombosis, and Vascular Biology, vol. 17, No. 10, pp. 2245-2249, Oct. 1997.

Morinaga, K. et al., "Development and Regression of Intimal Thickening of Arterially Transplanted Autologous Vein Grafts in Dogs," Journal of Vascular Surgery, vol. 5, No. 5, pp. 719-730, May 1987.

Nanjo, H. et al., "Intermitten Short-Duration Exposure To Low Wall Shear Stress Induces Intimal Thickening in Arteries Exposed To Chronic High Shear Stress," Experimental and Molecular Pathology, pp. 28-45, Apr. 7, 2005.

Ojha, M. et al., "Influence of Angle on Wall Shear Stress Distribution for an End-to-Side Anastomosis," Journal of Vascular Surgery, vol. 19, No. 6, pp. 1067-1073, Jun. 1994.

Ojha, M. "Spatial and Temporal Variations of Wall Shear Stress Within an End-to-Side Arterial Anastomosis Model," Journal of Biomechanics, vol. 26, No. 12, pp. 1377-11388, 1993.

Sarkar, S. et al., "The Mechanical Properties of Infrainguinal Vascular Bypass Grafts: Their Role in Influencing Patency," Journal of Vascular Endovascular Surgery, pp. 627-636, 2006.

\* cited by examiner

VASCULAR PROSTHESES

This U.S. non-provisional application claims benefit to and claims priority under 35 U.S.C. §119(a) to U.S. provisional application No. 60/939,250, filed May 21, 2007, and claims priority under 35 U.S.C. §119 to Swedish Patent Application No. 0701152-1, filed May 14, 2007.

FIELD OF THE INVENTION

The present invention relates to vascular prostheses, and more particularly to forked vascular prostheses with a defined geometrical shape for the treatment of obstructive vascular disease.

BACKGROUND OF THE INVENTION

Human mortality is predominantly related to atherosclerosis. Atherosclerotic stenoses are either treated with percutaneous transluminal angioplasty (balloon dilatation) or by-pass surgery. Today, 1.5 million revascularizations with these techniques are performed each year in the United States only. Approximately 40% of the patients experience a repeated narrowing within the first year due to restenosis or graft-stenosis, which in turn may induce a recurrence of organ ischemia with dramatic increased incidence of heart-infarction, amputation of legs and stroke. The cost in USA only for stenoses in grafts implanted in the legs is calculated to $100,000,000/year.

Graft-stenosis is due to intimal hyperplasia (IH). IH is characterized by migration and proliferation of smooth muscle cells followed by matrix deposition. IH can be regarded as an excessive response with scar tissue. Recent evidence has shown that hemodynamic, physical forces are the major contributors to the development of IH. Lowering of the shoving force exerted by the blood (shear stress) accelerates the development of IH in autologous vein grafts (Morinaga 1987), prosthetic grafts (Geary 1994) and in balloon-injured arteries (Bassiony 1998). Increased blood flow (increased shear stress) induces regression of established IH in grafts (Mattsson 1997). High variation in the level of shear stress may also increase the risk of IH (Nanjo 2006). Another hemodynamic factor of importance is turbulence. Increased turbulence raises the amount of IH (Fillinger 1989). The improved clinical handling of graft stenosis is therefore dependent on knowledge in both medical and physical sciences (Sarkar 2006).

Bypasses to treat stenoses are today implanted end-to-side to the artery (FIG. 2). This gives rise to a reduced shear stress at the "toe" and the "heal" of the connection sites, especially at the distal anastomosis (Ojha 1993; Ojha 1994) (FIG. 3). The development of IH is further supported by the fact that the suturing of the anastomoses co-localizes with the areas with low shear stress. The trauma imposed by the stitches in the vessel wall and the level of shear stress together induce cellular growth through different mechanisms, with IH to follow. Low shear stress will also be present at the division of flow in the recipient artery. Furthermore, the standard end-to side connection leads to a locally increased radius (FIG. 4). The level of shear stress decreases when the radius increases. The surgical procedure therefore leads to low shear stress and local induction of IH.

The standard by-pass graft also creates turbulent flow at the toe and the heal of the connection site. Turbulent flow is a known inducer of IH, (Fillinger 1989).

The end-to-side connection in bypass surgery faces other principal problems. It creates a bifurcation with a primary down-stream outflow and a secondary outflow. Since the artery has its given diameter, the two outflows have the same cross sectional area in spite of different need of blood flow. There is a splitting angle of 180 degrees between these "branches". These two constraints are part of the boundary conditions of the problem addressed by the present invention.

An improved graft should therefore be able to provide a high shear stress with as low variability as possible along with as low turbulence as possible. This will reduce the induction of IH and improve graft patency. Further aims of an improved bypass should be to minimize the needed driving pressure difference between the ends of the graft. This results in increased ability for the blood to flow through the conduit in presence of stenoses distal to the bypass. The separation of flow should be anatomically separated from the trauma by the stitches imposed by the surgery. The inducers of IH, hemodynamic factors and trauma, will thereby not be present together at the crucial connection site of the bypass to the recipient artery.

WO 2006/100659 describes vascular prostheses in the form of forked tubes. The disclosure however fails to provide a description of the geometrical features needed for a vascular prosthesis which provides a sufficiently high shear stress with a sufficiently low variability along with a sufficiently low turbulence to reduce the induction of IH and improve graft patency.

SUMMARY OF THE INVENTION

It is therefore an object of the present invention to provide a vascular prosthesis that alleviates the above-discussed problems of the prior art. This object is achieved by means of a vascular prosthesis according to the appended claims.

According to a first aspect of the invention there is provided a vascular prosthesis comprising a forked tube, having: an inflow tube with an inflow end; a primary distal outflow branch with a primary distal outflow end; and a secondary proximal outflow branch with a secondary proximal outflow end; the two outflow ends being directed in different directions; and the two outflow branches in the vicinity of the bifurcation having different cross-sectional areas; wherein the secondary proximal outflow branch is more curved than the primary distal outflow branch, and wherein the secondary proximal outflow branch in the vicinity of the bifurcation has a smaller cross-sectional area than the primary distal outflow branch.

In the context of this application, distal is used to denominate a direction away from the heart, and proximal to denominate a direction towards the heart.

With the new vascular prosthesis, an optimal relation between radii and angles can easily be achieved, as is discussed in more detail in the following. The new vascular prosthesis significantly reduces energy losses at the bifurcation, which evens out the level of shear stress, thereby avoiding areas with low shear stress and decreasing the tendency for turbulent flow. Since low shear stress and turbulent flow are well-known hemodynamic factors that induce graftstenosis, the risk for such complications is significantly reduced with the new vascular prosthesis.

In the vicinity of the bifurcation the ratio between the radius of the secondary proximal outflow branch (r) and the radius of the inflow tube ($\rho$) is preferably in the range 0.4 to 0.69, and most preferably in the range 0.45 to 0.65. In the vicinity of the bifurcation it is also preferred that the ratio between the radius of the primary distal outflow branch (R)

and the radius of the inflow tube ($\rho$) is in the range 0.7 to 1.0, and most preferably in the range 0.75 to 0.95.

The outflow angle ($\alpha$) from the inflow tube into the primary distal outflow branch is preferably in the range of 0 to 40 degrees, and more preferably in the range of 5 to 30 degrees, and most preferably in the range 8 to 25. Further, the outflow angle ($\beta$) from the inflow tube into the secondary proximal outflow branch is preferably in the range of 30 to 90 degrees, and more preferably in the range 40 to 70 degrees, and most preferably in the range 45 to 65 degrees.

Further, the radius of curvature ($r_c$) of the mid-sectional curve of the secondary outflow at all points is preferably greater than two times the radius of the inflow ($\rho$), and the radius of curvature ($r_c$) of the mid-sectional curve of the secondary outflow at the point where it has its lowest value is preferably less than six times the radius of the inflow ($\rho$).

Both outflow ends are preferably adapted to be connected to an artery with a radius in the range of 0.5 to 10 mm. Further, one or both of the outflow ends may be tapered to fit the recipient artery.

The secondary proximal outflow branch preferably has a gradually increasing cross-sectional area from the bifurcation to the outflow end. Hereby, a smooth transition is provided from a smaller cross-sectional area at the bifurcation to a larger cross-sectional area at the outflow end.

The outflow angle ($\beta$) from the inflow tube into the secondary proximal outflow end is preferably greater than the outflow angle ($\alpha$) from the inflow tube into the primary distal outflow end.

According to another aspect of the invention there is provided a method of performing a surgical procedure using a vascular prosthesis of the above-discussed type, the method comprising, in any order, the steps of:
a) cutting a recipient artery and separating the ends exposed by the cut;
b) suturing the primary distal outflow end of the vascular prosthesis to the down-stream end of the exposed artery;
c) suturing the secondary proximal outflow end of the vascular prosthesis to the up-stream end of the exposed artery; and
d) attaching the inflow end of the vascular prosthesis to a vessel for supply of blood through the vascular prosthesis to the recipient artery.

BRIEF DESCRIPTION OF THE DRAWINGS

The invention will be more clearly understood from the following description of some embodiments thereof, given by way of example only, with reference to the accompanying drawings, in which.

DETAILED DESCRIPTION OF THE INVENTION

The present invention provides a vascular prosthesis comprising: a forked tube, having an inflow tube with an inflow end; and a primary distal outflow branch with a primary distal outflow end, and a secondary proximal outflow branch with a secondary proximal outflow end; where the two outflow ends are directed in different directions; and where the two outflow branches initially have different cross-sectional areas; and where the secondary proximal outflow branch is more curved than the primary distal outflow branch.

Figure 5:
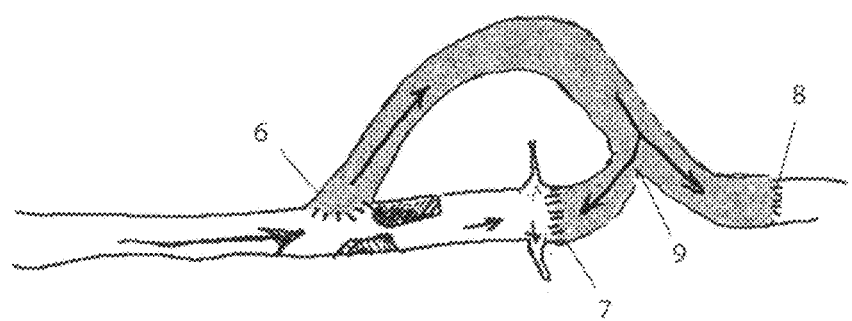
FIG. 5: A schematic illustration of the vascular prosthesis of the present invention in grey.

FIG. 5 illustrates an example of the vascular prosthesis of the present invention. The inflow end is attached via an ordinary "end-to-side" connection (6), but the primary distal outflow end (8) and the secondary proximal outflow end (7) are connected "end-to-end" to the recipient artery. The flow dividing bifurcation (9) is included in the graft. The two outflow branches initially have different cross-sectional areas, i.e. the two outflow branches have different cross-sectional areas directly following the point where the vascular prosthesis divides into two branches, i.e. in direct connection to the bifurcation point.

Figure 8:
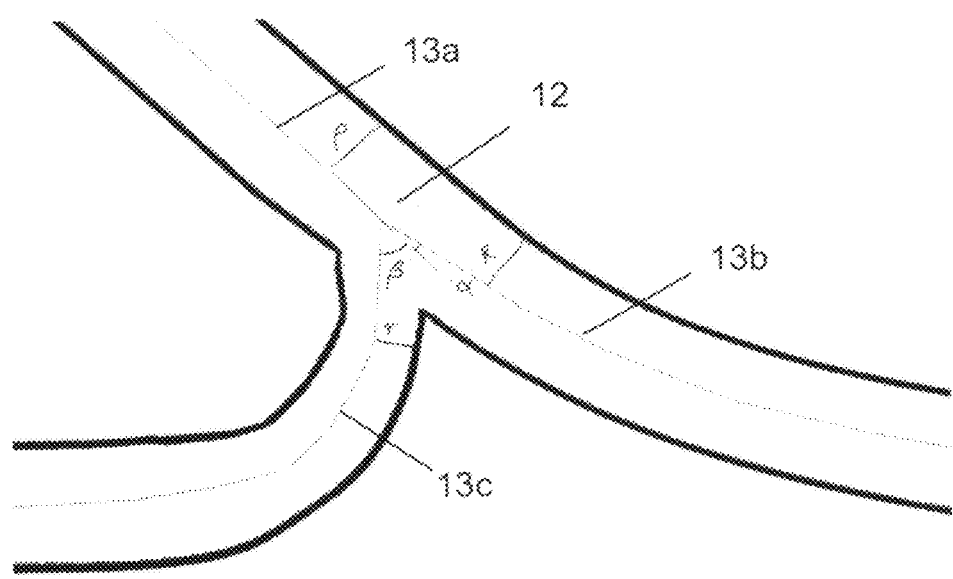
FIG. 8: Illustration of the relations between the radius, and the angles, at the bifurcation point in the vascular prosthesis of the present invention.

The ratio between the radius of the secondary proximal outflow (r in FIG. 8) and the radius of the inflow ($\rho$ in FIG. 8), and the ratio between the radius of the primary distal outflow (R in FIG. 8) and the radius of the inflow, respectively, are advantageous features of the vascular prosthesis of the present invention. FIG. 8 illustrates the relations between the radii, and the angles, at the bifurcation point in the vascular prosthesis according to an embodiment of the present invention. The inflow of the tubular vessel is splitting into two branches, the primary distal outflow with a radius of R, and the secondary proximal outflow with a radius of r. The radius R of the primary distal outflow branch and the radius r of the secondary proximal outflow branch are measured directly following the point where the vascular prosthesis divides into two branches, i.e. in direct connection to the bifurcation point.

The different radii and cross-sectional areas at different points of the vascular prosthesis are measured on the inside of the vascular prosthesis.

The inflow has a radius of $\rho$. The angles are measured at the bifurcation point and are given by $\alpha$ for the primary distal outflow, and by $\beta$ for the secondary outflow. The bifurcation point (12) is defined as the point where the mid-sectional curve of the upstream tubular vessel splits into two outflows. Note that the angle between those outflows is $\alpha+\beta$.

The relations of the radii in FIG. 8 are preferably given by the following ratios:

$0.7 < R/\rho < 1$ $0.4 < r/\rho < 0.69$

Alternatively $R/\rho = 0.85 \pm 0.15$ $r/\rho = 0.55 \pm 0.15$

The angles are given in degrees as $\alpha = 20° \pm 20°$ and $\beta = 60° \pm 30°$ The ratio between the radius of the secondary proximal outflow (r) and the radius of the inflow ($\rho$), and the ratio between the radius of the primary distal outflow (R) and the radius of the inflow ($\rho$), respectively, are advantageous features of the vascular prosthesis of the present invention.

Accordingly, in one embodiment of the present invention the vascular prosthesis is characterized by the ratio between the radius of the secondary proximal outflow (r) and the radius of the inflow ($\rho$) being in the range 0.4 to 0.69.

In another embodiment of the present invention the vascular prosthesis is further characterized by the ratio between the radius of the primary distal outflow (R) and the radius of the inflow ($\rho$) being in the range 0.7 to 1.0.

The concept of radius is used in a generalized sense, such that the radius of a non-circular cross-section, is defined as the radius of a disc with the same cross-sectional area.

In one preferred embodiment of the present invention the vascular prosthesis is characterized by the ratio between the radius of the secondary proximal outflow (r) and the radius of the inflow ($\rho$) is in the range 0.45 to 0.65, more specifically in the range 0.5 to 0.62, and/or the ratio between the radius of the primary distal outflow (R) and the radius of the inflow ($\rho$) is in the range 0.75 to 0.95, more specifically in the range 0.8 to 0.95.

Consequently, in the vascular prosthesis according to present invention the cross-sectional area of the primary distal outflow is initially (i.e. in the vicinity of the bifurcation) larger than the cross-sectional area of the secondary proximal outflow giving priority to the main down-stream flow in the primary distal outflow.

According to this embodiment of the present invention the vascular prosthesis preferably has a ratio between the primary distal outflow cross-sectional area and the secondary proximal outflow cross-sectional area which is greater than 1, and preferably greater than 2.

The primary distal outflow angle ($\alpha$ in FIG. 8) and the secondary proximal outflow angle ($\beta$ in FIG. 8), are further advantageous features of the vascular prosthesis of the present invention.

The primary distal outflow angle ($\alpha$) is measured as the angle between the mid-sectional curve of the inflow tract (13a) and the mid-sectional curve of the primary distal outflow tract (13b) at the bifurcation point. The secondary distal outflow angle ($\beta$) is measured as the angle between the mid-sectional curve of the inflow tract (13a) and the mid-sectional curve of the secondary distal outflow tract (13c) at the bifurcation point. The bifurcation point is defined as the point where the mid-sectional curve of the up-stream tubular vessel is splitting into two branches.

In another embodiment of the present invention the vascular prosthesis is characterized by the primary distal outflow angle ($\alpha$) being in the range of 0 to 40 degrees, such as in the range of 5 to 30 degrees, or more specifically in the range 8 to 25 degrees; and the secondary proximal outflow angle ($\beta$) being in the range of 30 to 90 degrees, such as in the range 40 to 70-degrees, or more specifically in the range 45 to 65 degrees.

In one preferred embodiment the primary distal outflow angle ($\alpha$) is 10 degrees. In another preferred embodiment the secondary proximal outflow angle ($\beta$) is 50 degrees.

In another embodiment of the present invention the vascular prosthesis is characterized by the primary distal outflow and/or the secondary proximal outflow having a defined curvature.

Figure 9:
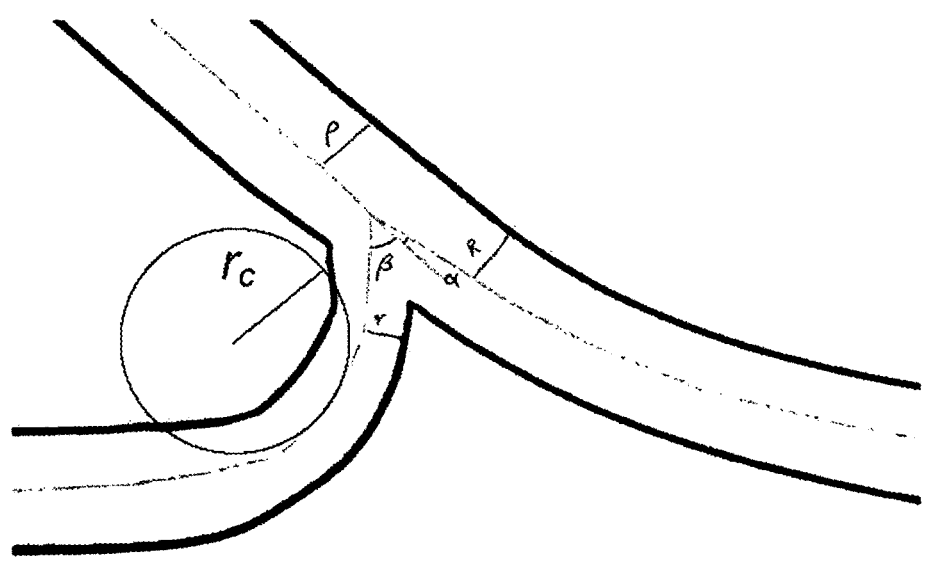
FIG. 9: Illustration of the relation between the radius of curvature $r_c$ of the mid-sectional curve of the secondary outflow, and the radius $\rho$ of the inflow.

FIG. 9 illustrates the relation between the radius of curvature ($r_c$) of the mid-sectional curve of the secondary outflow, and the radius of the inflow ($\rho$). Following the mid-sectional curve at the secondary outflow, its radius of curvature can be estimated by fitting an osculating circle along that curve. The radius of curvature at a certain point is defined as the radius of the osculating circle at that point. The osculating circle with the smallest radius can be found at the point where the mid-sectional curve has the highest curvature. The radius of curvature of the mid-sectional curve of the secondary proximal outflow ($r_c$), is a further advantageous feature of the vascular prosthesis of the present invention. The radius of curvature of the mid-sectional curve of the secondary proximal outflow ($r_c$) is always greater than two times the radius of the inflow ($\rho$). Thus there is a maximal allowed curvature of the secondary proximal outflow. At the point where the radius of curvature of the mid-sectional curve of the secondary outflow ($r_c$) has its lowest value it is less than 6 times the radius of the inflow ($\rho$). Thus there is a minimal allowed curvature of the secondary proximal outflow.

In yet another embodiment of the present invention the vascular prosthesis is characterized by the radius of curvature of the mid-sectional curve of the secondary proximal outflow ($r_c$) at all points being greater than two times the radius of the inflow ($\rho$), and the radius of curvature of the mid-sectional curve of the secondary outflow ($r_c$) at the point where it has its lowest value is less than 6 times the radius of the inflow ($\rho$).

In one preferred embodiment of the present invention the vascular prosthesis is characterized by the ratio between the radius of curvature of the mid-sectional curve of the secondary proximal outflow ($r_c$) and radius of the inflow ($\rho$) at all points being greater than 2, such as greater than 3.

In a preferred embodiment of the present invention two or more of the features characterizing the vascular prosthesis according to present invention as defined above are combined.

Accordingly, in one preferred embodiment the present invention provides a vascular prosthesis comprising a forked tube having an inflow, and a primary distal outflow, and a secondary proximal outflow characterized by;

a) the ratio between the radius of the secondary proximal outflow (r) and the radius of the inflow ($\rho$) being in the range 0.4 to 0.69, such as in the range 0.45 to 0.65, or more specifically in the range 0.5 to 0.62, and the ratio between the radius of the primary distal outflow (R) and/or the radius of the inflow ($\rho$) being in the range 0.7 to 1.0, such as in the range 0.75 to 0.95, or more specifically in the range 0.8 to 0.95;

b) the primary distal outflow angle ($\alpha$) being in the range of 0 to 40 degrees, such as in the range of 5 to 30, or more specifically in the range 8 to 25;

c) the secondary proximal outflow angle ($\beta$) being in the range of 30 to 90 degrees, such as in the range 40 to 70 degrees, or more specifically in the range 45 to 65 degrees; and/or d) the radius of curvature of the mid-sectional curve of the secondary proximal outflow ($r_c$) at all points being greater than two times the radius of the inflow ($\rho$), and the radius of curvature of the mid-sectional curve of the secondary outflow ($r_c$) at the point where it has its lowest value is less than 6 times the radius of the inflow ($\rho$).

Both outflow endings of the vascular prosthesis of the present invention can be adapted to be connected to an artery with a radius in the range of 0.5 to 10 mm. Consequently, the radius of the inflow ($\rho$) of the vascular prosthesis of the invention can be in the range of 0.5 to 10 mm.

The walls of the vascular prosthesis can have a thickness of 0.01 to 3 mm, preferably. The thickness of the walls of the vascular prosthesis can vary between different parts of the prosthesis to allow a maximum stability at the bifurcation and allow for more easy suturing at the inflow and outflow ends.

The inflow and outflow ends can be reinforced to allow for sufficiently efficient retention of the sutures.

Both outflow endings of the vascular prosthesis of the present invention can be adapted for end-to-end anastomoses with the host artery.

In one embodiment of the present invention one or both of the outflow endings of the vascular prosthesis are tapered to fit the recipient artery. The endings can be tapered inwardly or outwardly. The term tapered is used to define that radius of the outflow ending is gradually increasing or decreasing.

The vascular prostheses according to the present invention provide a high shear stress with a low variability along with a low turbulence. This will reduce the induction of IH and improve graft patency. The vascular prostheses according to the present invention further minimize the needed driving pressure difference between the ends of the graft. This results in increased ability for the blood to flow through the conduit in presence of stenoses distal to the bypass. The separation of flow is anatomically separated from the trauma by the stitches imposed on the recipient artery by the surgery. The inducers of IH, hemodynamic factors and trauma, will thereby not be present together at the crucial connection site of the bypass to the recipient artery.

The present invention further provides a method of performing a surgical procedure using a vascular prosthesis according to the invention, the method comprising any order of the steps a) cutting a recipient artery and separating the ends exposed by the cut;
b) suturing the primary distal outflow end of the vascular prosthesis to the down-stream end of the exposed artery;
c) suturing the secondary proximal outflow end of the vascular prosthesis to the up-stream end of the exposed artery; and
d) attaching the inflow end of the vascular prosthesis to a vessel for supply of blood through the vascular prosthesis to the recipient artery.

Design of Preferred Embodiments

In a preferred design, we have locally at the bifurcation point, utilized Murray's law (Murray 1926a, Murray 1926b, Zamir 1978, and Woldenberg et al 1986), which defines the optimal relation between radii and angles (see FIG. 8) causing minimal energy losses at flow bifurcations and also evens out the level of shear stress to avoid areas with low shear stress (FIG. 7) and decreases the tendency for turbulent flow. The bypass situation however differs from an ideal flow situation as defined by Murray's law. A bypass has outflows in opposite directions. The recipient artery has the same cross sectional area, even if priority of the blood flow should be given to the distal primary outflow. This preferred design is a balance between an optimal flow division, an effective redirection of the outflows with a controlled curvature of the tapered secondary outflow (FIG. 9), keeping our overall aim in focus to reduce the variability of shear stress, lowering of turbulence and lowering the need for higher pressure differences over the graft.

Figure 1:
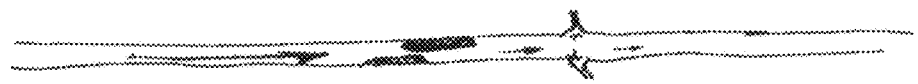
FIG. 1: Illustration of an atherosclerotic artery.
Figure 2:
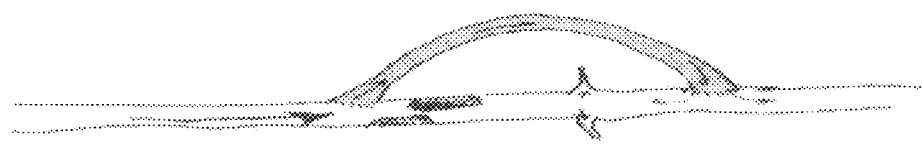
FIG. 2: Illustration showing a standard by-pass graft according to the prior art. Both the up-stream and the down-stream attachments are "end-to-side".
Figure 3:
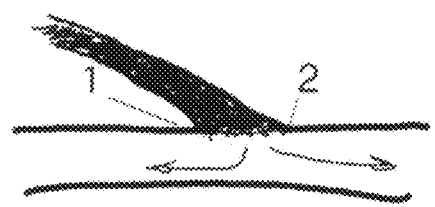
FIG. 3: Illustration defining the "heel" (1) and the "toe" (2) in a vascular anastomosis according to the prior art.
Figure 4:
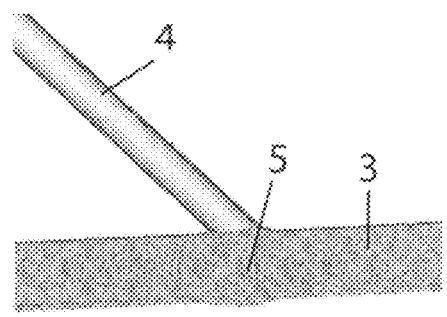
FIG. 4: Illustration of a standard "end-to-side" connection according to the prior art. The illustration shows the recipient artery (3) and the graft (4). Note the expanded diameter at the attachment site (5) due to the added material (the graft).

Furthermore, by using the vascular prostheses of the present invention in a surgical procedure the trauma by suturing of the graft is anatomically separated from the bifurcation of flow (see FIGS. 3 and 5). This leads to a separation of the two different inducers of cellular proliferation; trauma with secondary inflammation and hemodynamic disturbances.

Furthermore, the present invention has low energy loss, which thereby preserves the blood pressure present proximal to the bypass. The present invention has optimized the flow conditions in the whole graft, not only at the anastomoses to the recipient artery, see FIG. 6. The present invention provides a design where, at the bifurcation point, the two outflows have different cross-sectional areas and the outflow branches have bounded curvatures. We have reached the above characteristics by application of the principles in Murray's law. These principles form the basis of the new approved and unique design of the vascular prostheses of the present invention.

Computer Simulations

Figure 6:
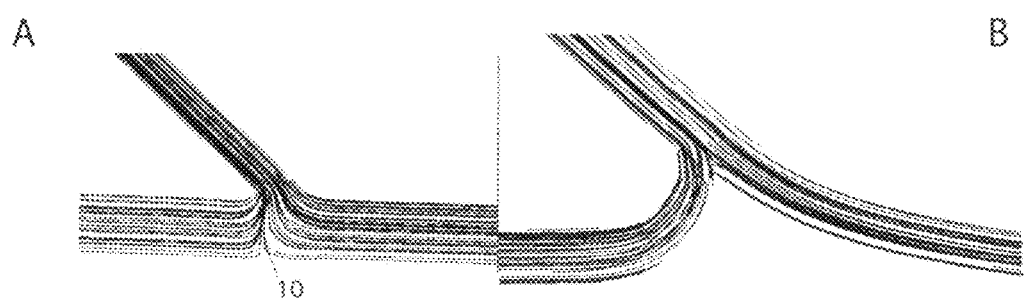
FIG. 6: Result of a computer simulation of blood flow stream through a standard graft compared to the flow through the vascular prosthesis of the present invention. Panel A: Blood flow in a standard by-pass graft. Panel B: Blood flow in the vascular prosthesis of the present invention.

The vascular prostheses of the present invention have a number of properties that makes them an improvement in comparison to the prostheses available today. To illustrate the improvements we have performed computer simulations as comparative studies, using a finite element scheme in three dimensions. FIG. 6 shows the result of a computer simulation of blood flow stream through a standard graft compared to the flow through the vascular prosthesis of the present invention. Panel A: Blood flow in a standard by-pass graft. Note the flow-divider at the opposite side of the graft outlet in the artery (10). Panel B: Blood flow in the vascular prosthesis of the present invention. Note the lack of flow divider with areas of low flow. Note the smoothly curved flow lines.

Figure 7:
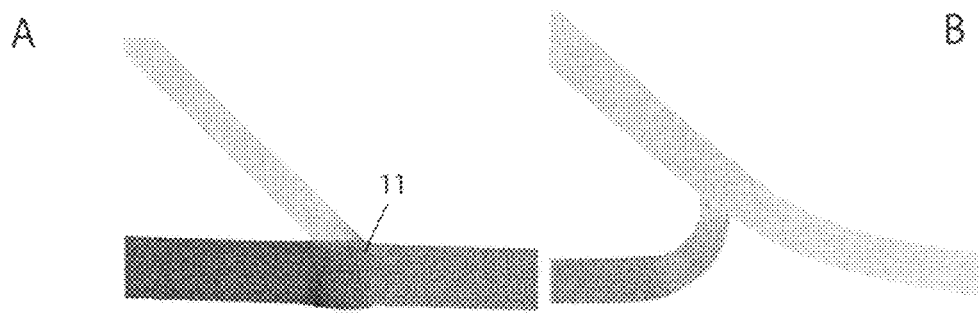
FIG. 7: Result of a computer simulation of the level of shear stress through a standard graft and the new vascular prosthesis. The darker the colour the lower the shear stress. The same pressure difference has been used over the two grafts. Panel A: Shear stress in a standard by-pass graft. Panel B: Shear stress in the vascular prosthesis of the present invention.

FIG. 7 shows the result of a computer simulation of the level of shear stress through a standard graft and the new vascular prosthesis. The darker the colour the lower the shear stress. The same pressure difference has been used over the two grafts. Panel A: Shear stress in a standard by-pass graft. Note a lower level of shear stress compared to the vascular prosthesis of the present invention. Note the high variability of shear stress. Note the diameter expansion of the artery at the insertion site of the graft (11). Panel B: Shear stress in the vascular prosthesis of the present invention. Note a higher level of shear stress. Note the low variability of shear stress. Note the lack of local diameter variation at the connection sites.

These simulations clearly demonstrate that the vascular prostheses of the invention provide:

Higher shear stress in the outflows (FIG. 7)
A reduced variability of shear stress (FIG. 7)
Lack of very low shear stress at the flow-dividing point (FIG. 7)
No changes in radius of the recipient artery at the connection sites (FIG. 7)
Less prone to turbulent flow (FIG. 6)
At the bifurcation there is a difference in the cross sectional area between the outflow tracts, giving priority to the main down-stream tract. The secondary proximal outflow end is tapered to fit the common diameter of the recipient artery The higher levels of shear stress present at the same degree of pressure difference is equivalent to a more energy effective graft A design using optimal angles related to flow and diameters at the bifurcation point Material The vascular prostheses of the present invention are not limited to any materials, but are preferable made of a biocompatible material. The material should further enable the prostheses to adopt and maintain its intended geometrical shape under physiological conditions after implantation. The material can be a fluoroplastic material such as expanded polytetrafluoroethylene (ePTFE), tetrafluoroethylene perfluoroalkyl vinyl ether copolymer, tetrafluoroethylenehexafluoropolypropylene copolymer, or tetrafluoroethylene ethylene copolymer. The material can also be a polyester such as Dacron. The material can also be a rubbery material such as ethylene-propylene copolymer, polyurethane, nitrile rubber, chlorinated polyisoprene, acryl rubber, butyl rubber, and halogenated butyl rubber, and rubbery elastomers such as ethylene-vinyl acetate type elastomer, butadiene type elastomer, amide type elastomer, ester type elastomer, urethane type elastomer, alpha-olefin type elastomer, and styrene type elastomer.

The material should preferably have antithrombogenicity by itself. If the material has no or little antithrombogenicity, then a layer made of antithrombotic material may be disposed on the inner surface of the prostheses, or the prostheses itself may carry an antithrombotic material. The antithrombotic material is not limited to any particular material, but may be heparin, collagen, gelatine, urokinase, fibrin, aspirin, or a prostacyclin based material.

The material of the vascular prostheses of the present invention can also be made of textile materials composed of monofilament fibers and composite fibers. Composite fibers are fibers manufactured by causing two or more polymers of differing qualities discharged in independently controlled amounts, combined with one another in one and the same spinneret, and simultaneously spun. The composite fiber can be composed of polyethylene terephthalate containing a polyester fiber exhibiting outstanding stability in the living body and a polyester elastomer. The polyesters include, for example, polybutylene terephthalate, polyester-polyether block copolymer, and polyester-polyester copolymer. The polyesterpolyester copolymer elastomers include aliphatic polyesters such as polyethylene terephthalate, polyethylene terephthalate/-isophthalate, or poly(1,4-cyclohexane dimethylene terephthalate).

The vascular prostheses of the invention can be constructed by subjecting the fibers mentioned above to one or more of weaving, knitting, expansion and braiding treatments, for example.

The vascular prostheses of the invention can be constructed by a combination of weaving, knitting or braiding of fibrous material, and molding or casting of plastic, rubber, or polymeric material.

The vascular prostheses of the invention can be reinforced to assist it in maintaining its geometrical shape. The reinforcement may be integral with or adherent to the wall of the prostheses, for example comprising a helical winding.

REFERENCES

Bassiouny H S, Song R H, Hong X F, Singh A, Kocharyan H and Glagov S. Flow regulation of 72-kD collagenase IV (MMP-2) after experimental arterial injury. Circulation 1998; 98:157-63.

Fillinger M F, Reinitz E R, Schwartz R A, Resetarits D E, Paskanik A M, Bredenberg C E. Beneficial effects of banding on venous intimal-medial hyperplasia in arteriovenous loop grafts. Am. J. Surg. 1989; 158(2):87-94

Geary R L, Kohler T R, Vergel 5, Kirkman T R and Clowes A W. Time course of flow induced smooth muscle cell proliferation and intimal thickening in endothelialized baboon vascular grafts. Circ. Res. 1994; 74:14-23.

Mattsson E J, Kohler T R, Vergel S M and Clowes A W. Increased blood flow induces regression of intimal hyperplasia. Arterioscler. Thromb. Vasc. Biol. 1997; 17:2245-9

Morinaga K, Eguchi H, Miyazaki T, Okadome K and Sugimachi K. Development and regression of intimal thickening of arterially transplanted autologous vein grafts in dogs. J. Vasc. Surg. 1987; 5:719-30.

Murray C D. The physiological principle of minimum work applied to the angle of branching of arteries. J. Gen. Phys. 1926; 9, 835-841.

Murray C D. The physiological principle of minimum work. I. The vascular system and the cost of blood volume. Proc. Natl. Acad. Sci. USA. 1926; 12, 207-214.

Nanjo H, Sho E, Komatsu M, Sho M, Zarins C K, Masuda H. Intermittent short-duration exposure to low wall shear stress induces intimal thickening in arteries exposed to chronic high shear stress. Exp. Mol. Pathol. 2006; 80(1): 38-45.

Ojha M, Cobbold R S, Jobnston K W. Influence of angle on wall shear stress distribution for an end-to-side anastomosis. J. Vasc. Surg. 1994; 19(6): 1067-73.

Ojha M. Spatial and temporal variations of wall shear stress within an end-to-side arterial anastomosis model. J. Biomech. 1993; 26(12):1377-88.

Sarkar S, Salacinski H J, Hamilton G, Seifalian A M. The mechanical properties of infrainguinal vascular bypass grafts: their role in influencing patency. Eur. J. Vasc. Endovasc. Surg. 2006; 1(6):627-36.

Woldenberg M J and Horsfield K. Relation of branching angles to optimality for four cost principles. J. Theor. Biol. 1986; 122(2):187-204.

Zamir M. Nonsymmetrical bifurcations in arterial branching. J. Gen. Phys. 1978; 72, 837-845.

The invention claimed is:

1. A vascular bypass prosthesis for treatment of obstructive vascular disease having a forked tube, comprising:
an inflow tube with an inflow end;
a primary distal outflow branch including a primary distal outflow end; and
a secondary proximal outflow branch including a secondary proximal outflow end;
wherein the primary distal outflow branch and the secondary proximal outflow branch divide into different directions creating a bifurcation, and in vicinity of the bifurcation, the primary distal outflow branch and the secondary proximal outflow branch have different cross-sectional areas,
wherein the secondary proximal outflow branch is more curved than the primary distal outflow branch, and an angle of outflow from the inflow tube to the secondary proximal outflow branch, at the bifurcation, is in the range of 30 to 90 degrees measured between a center of axis of the inflow tube and a center of axis of the secondary proximal outflow branch, and
wherein the secondary proximal outflow branch in the vicinity of the bifurcation has a smaller cross-sectional area than the primary distal outflow branch, and the secondary proximal outflow branch has a gradual increasing cross-sectional area from the bifurcation to the secondary proximal outflow end.

2. The vascular prosthesis according to claim 1, wherein, in the vicinity of the bifurcation, a ratio between a radius of the secondary proximal outflow branch and a radius of the inflow tube is in a range of 0.4 to 0.69.

3. The vascular prosthesis according to claim 2, wherein, in the vicinity of the bifurcation, the ratio between the radius of the secondary proximal outflow branch and the radius of the inflow tube is in the range of 0.45 to 0.65.

4. The vascular prosthesis according to claim 1, wherein, in the vicinity of the bifurcation, a ratio between a radius of the primary distal outflow branch and a radius of the inflow tube is in a range of 0.7 to 1.0.

5. The vascular prosthesis according to claim 4, wherein, in the vicinity of the bifurcation, the ratio between the radius of the primary distal outflow branch and the radius of the inflow tube is in the range of 0.75 to 0.95.

6. The vascular prosthesis according to claim 1, wherein an angle of outflow from the inflow tube into the primary distal outflow branch is in a range of 0 to 40 degrees.

7. The vascular prosthesis according to claim 6, wherein the angle of outflow from the inflow tube into the primary distal outflow branch is in the range of 5 to 30 degrees.

8. The vascular prosthesis according to claim 7, wherein the angle of outflow from the inflow tube into the primary distal outflow branch is in the range of 8 to 25 degrees.

9. The vascular prosthesis according to claim 1, wherein an angle of outflow from the inflow tube into the secondary proximal outflow branch is in a range of 40 to 70 degrees.

10. The vascular prosthesis according to claim 9, wherein the angle of outflow from the inflow tube into the secondary proximal outflow branch is in the range of 45 to 65 degrees.

11. The vascular prosthesis according to claim 1, wherein a radius of curvature of a mid-sectional curve of the secondary proximal outflow branch at all points is greater than two times a radius of the inflow tube.

12. The vascular prosthesis according to claim 1, wherein both outflow ends are adapted to be connected to an artery with a radius in a range of 0.5 to 10 mm.

13. The vascular prosthesis according to claim 1, wherein at least one of the outflow ends are tapered to fit the recipient artery.

14. The vascular prosthesis according to claim 1, wherein an angle of outflow from the inflow tube into the secondary proximal outflow end is greater than the angle of outflow from the inflow tube into the primary distal outflow end.

15. A method of performing a surgical procedure using the vascular prosthesis according to claim 1, the method comprising, in any order, the steps of:
 cutting a recipient artery and separating the ends thereof exposed by the cut;
 suturing the primary distal outflow end of the vascular prosthesis to a down-stream end of the exposed artery;
 suturing the secondary proximal outflow end of the vascular prosthesis to an up-stream end of the exposed artery; and
 attaching the inflow end of the vascular prosthesis to a vessel for supply of blood through the vascular prosthesis to the recipient artery.

16. The vascular prosthesis according to claim 1, wherein a radius of curvature of a mid-sectional curve of the secondary proximal outflow branch at a point of having its lowest value is less than six times a radius of the inflow tube.

17. The vascular prosthesis according to claim 1, wherein a radius of curvature of a mid-sectional curve of the secondary proximal outflow branch at all points is greater than three times a radius of the inflow tube.

18. The vascular prosthesis according to claim 1, wherein at least one of the outflow ends is tapered to fit a recipient artery.

19. The vascular prosthesis according to claim 18, wherein the at least one of the outflow ends taper inwardly.

20. The vascular prosthesis according to claim 18, wherein the at least one of the outflow ends taper outwardly.

21. A vascular by-pass prosthesis for treatment of obstructive vascular disease having a forked tube, comprising:
 an inflow tube with an inflow end;
 a primary distal outflow branch including a primary distal outflow end; and
 a secondary proximal outflow branch including a secondary proximal outflow end,
 wherein the primary distal outflow branch and the secondary proximal outflow branch divide into different directions creating a bifurcation, and in vicinity of the bifurcation, the primary distal outflow branch and the secondary proximal outflow branch have different cross-sectional areas, a ratio between the radius of the secondary proximal outflow branch and the radius of the inflow tube being in a range of 0.4 to 0.69, and a ratio between a radius of the primary distal outflow branch and a radius of the inflow tube being in a range of 0.7 to 1.0,
 wherein the secondary proximal outflow branch is more curved than the primary distal outflow branch, and an angle of outflow from the inflow tube to the secondary proximal outflow branch, at the bifurcation, is in the range of 30 to 90 degrees measured between a center of axis of the inflow tube and a center of axis of the secondary proximal outflow branch, and
 wherein the secondary proximal outflow branch in the vicinity of the bifurcation has a smaller cross-sectional area than the primary distal outflow branch, and the secondary proximal outflow branch has a gradual increasing cross-sectional area from the bifurcation to the secondary proximal outflow end.

22. A vascular bypass prosthesis for treatment of obstructive vascular disease having a forked tube, comprising:
 an inflow tube with an inflow end;
 a primary distal outflow branch including a primary distal outflow end; and
 a secondary proximal outflow branch including a secondary proximal outflow end;
 wherein the primary distal outflow branch and the secondary proximal outflow branch divide into different directions creating a bifurcation, and in vicinity of the bifurcation, the primary distal outflow branch and the secondary proximal outflow branch have different cross-sectional areas,
 wherein the secondary proximal outflow branch is more curved than the primary distal outflow branch, and an angle between a center axis of the inflow tube and a center axis of the secondary proximal outflow branch, at the bifurcation, is in the range of 30 to 90 degrees, and
 wherein the secondary proximal outflow branch in the vicinity of the bifurcation has a smaller cross-sectional area than the primary distal outflow branch, and the secondary proximal outflow branch has a gradual increasing cross-sectional area from the bifurcation to the secondary proximal outflow end.

23. The vascular prosthesis according to claim 1, wherein the vascular bypass prosthesis forms an monolithic unit.

* * * * *